(12) United States Patent
Stueven et al.

(10) Patent No.: US 7,951,304 B2
(45) Date of Patent: May 31, 2011

(54) METHOD FOR PRODUCING MECHANICALLY STABLE WATER-ABSORBENT POLYMER PARTICLES

(75) Inventors: Uwe Stueven, Bad Soden (DE); Rüdiger Funk, Niedernhausen (DE); Matthias Weismantel, Jossgrund (DE); Wilfried Heide, Freinsheim (DE); Marco Krüger, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/520,419

(22) PCT Filed: Dec. 12, 2007

(86) PCT No.: PCT/EP2007/063758
§ 371 (c)(1),
(2), (4) Date: Sep. 22, 2009

(87) PCT Pub. No.: WO2008/077780
PCT Pub. Date: Jul. 3, 2008

(65) Prior Publication Data
US 2010/0019198 A1    Jan. 28, 2010

(30) Foreign Application Priority Data

Dec. 22, 2006  (EP) .................................... 06126998

(51) Int. Cl.
| | |
|---|---|
| C09K 3/00 | (2006.01) |
| B05D 7/00 | (2006.01) |
| B05D 1/40 | (2006.01) |
| B05D 3/02 | (2006.01) |
| B32B 19/00 | (2006.01) |
| B01J 19/00 | (2006.01) |
| C08F 2/00 | (2006.01) |
| C08G 85/00 | (2006.01) |
| B01J 20/26 | (2006.01) |
| C08L 15/00 | (2006.01) |

(52) U.S. Cl. ........ 252/194; 522/153; 427/212; 427/331; 427/388.4; 428/357; 422/131; 526/72; 502/402; 523/111

(58) Field of Classification Search .................. 252/194; 522/153; 427/212, 331, 388.4; 428/357; 422/131; 526/72; 502/402; 523/111
See application file for complete search history.

(56) References Cited

U.S. PATENT DOCUMENTS

| | | |
|---|---|---|
| 5,269,980 A | 12/1993 | Levendis et al. |
| 5,731,365 A | 3/1998 | Engelhardt et al. |
| 5,840,321 A | 11/1998 | Engelhardt et al. |
| 6,414,214 B1 | 7/2002 | Engelhardt et al. |
| 2006/0217508 A1 | 9/2006 | Schmid et al. |
| 2007/0100115 A1 | 5/2007 | Schmid et al. |
| 2007/0244280 A1 | 10/2007 | Losch et al. |
| 2008/0045624 A1 | 2/2008 | Losch et al. |
| 2008/0045625 A1 | 2/2008 | Losch et al. |
| 2008/0188586 A1 | 8/2008 | Bruhns et al. |
| 2008/0188821 A1 | 8/2008 | Losch et al. |
| 2008/0194778 A1 | 8/2008 | Losch et al. |

FOREIGN PATENT DOCUMENTS

| | | |
|---|---|---|
| DE | 103 14 466 A1 | 10/2004 |
| DE | 103 40 253 A1 | 3/2005 |
| DE | 10 2004 024 437 A1 | 12/2005 |
| DE | 10 2004 042 946 A1 | 3/2006 |
| DE | 10 2004 042 948 A1 | 3/2006 |
| DE | 10 2004 042 955 A1 | 3/2006 |
| DE | 10 2005 002 412 A1 | 7/2006 |
| DE | 10 2005 019 398 A1 | 10/2006 |
| EP | 0 348 180 A2 | 12/1989 |
| EP | 703 265 A1 | 3/1996 |
| EP | 755 964 A2 | 1/1997 |
| WO | WO-96/40427 A1 | 12/1996 |
| WO | WO-01/25290 A1 | 4/2001 |
| WO | WO-2006/079631 A1 | 8/2006 |

OTHER PUBLICATIONS

Buchholz et al., *Modern Superabsorbent Polymer Technology*, Wiley-VCH, 71-103 (1998).
Deutsche Anmeldung mit dem Aktenzeichen 10 2006 001 596.7.
International Search Report and Written Opinion in PCT/EP2007/063758 dated Apr. 2, 2008.

*Primary Examiner* — Lorna M Douyon
*Assistant Examiner* — Tanisha Diggs
(74) *Attorney, Agent, or Firm* — Marshall, Gerstein & Borun LLP

(57) ABSTRACT

A process for producing water-absorbing polymer particles by polymerizing droplets of a monomer solution in a gas phase surrounding the droplets and postcrosslinking the polymer particles, wherein the postcrosslinked polymer particles are at least partly coated.

15 Claims, No Drawings

METHOD FOR PRODUCING MECHANICALLY STABLE WATER-ABSORBENT POLYMER PARTICLES

CROSS-REFERENCE TO RELATED APPLICATIONS

This is the U.S. national phase of International Application No. PCT/EP2007/063758, filed Dec. 12, 2007, which claims the benefit of European Patent Application No. 06126998.1, filed Dec. 22, 2006.

The present invention relates to a process for producing water-absorbing polymerparticles by polymerizing droplets of a monomer solution in a gas phase surrounding the droplets and postcrosslinking the polymer particles, wherein the postcrosslinked polymer particles are at least partly coated.

The preparation of water-absorbing polymer particles is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymer are used to produce diapers, tampons, sanitary napkins and other hygiene articles, but also water-retaining agents in market gardening.

The properties of the water-absorbing polymers can be adjusted via the degree of crosslinking. With increasing degree of crosslinking, the gel strength rises and the absorption capacity falls.

To improve the use properties, for example saline flow conductivity in a swollen gel bed (SFC) in the diaper and absorption under pressure (AUP), water-absorbing polymer particles are generally postcrosslinked. As a result, only the degree of crosslinking of the particle surface rises, as a result of which the absorption under pressure (AUP) and the centrifuge retention capacity (CRC) can be at least partly decoupled. This postcrosslinking can be performed in the aqueous gel phase. However, dried, ground and screened-off polymer particles (base polymer) are preferably coated on the surface with a post crosslinker, thermally postcrosslinked and dried. Crosslinkers suitable for this purpose are compounds which comprise groups which can form covalent bonds with the carboxylate groups of the hydrophilic polymer.

Spray polymerization allows the process steps of polymerization and drying to be combined. In addition, the particle size can be set within certain limits by virtue of suitable process control.

The production of water-absorbing polymer particles by polymerizing droplets of a monomer solution is described, for example, in EP 348 180 A1, WO 96/40427 A1, U.S. Pat. No. 5,269,980, DE 103 14 466 A1, DE 103 40 253 A1, DE 10 2004 024 437 A1 and DE 10 2005 002 412 A1, and also the prior German application 102006001596.7.

DE 10 2004 042 946 A1, DE 10 2004 042 948 A1, DE 10 2004 042 955 A1 and DE 10 2005 019 398 A1 describe the production of thickeners by spray polymerization.

WO 2006/079631 A1 describes a process for dropletization polymerization, wherein the polymer particles are dried in a fluidized bed and optionally postcrosslinked.

EP 703 265 A1 describes a process for improving the attrition resistance of water-absorbing polymer particles by coating with film-forming polymers.

EP 755 964 A2 likewise discloses a process for improving the attrition resistance of water-absorbing polymer particles by coating the particles with waxes.

It was an object of the present invention to provide an improved process for producing water-absorbing polymer particles by polymerizing droplets of a monomer solution in a gas phase surrounding the droplets.

The object was achieved by a process for producing water-absorbing polymer particles by polymerizing droplets of a monomer solution comprising
a) at least one ethylenically unsaturated monomer,
b) optionally at least one crosslinker,
c) at least one initiator,
d) water,
in a gas phase surrounding the droplets, the resulting polymer particles being postcrosslinked, which comprises at least partly coating the postcrosslinked polymer particles.

Polymerization of monomer solution droplets in a gas phase surrounding the droplets ("dropletization polymerization") affords round polymer particles of high mean sphericity (mSPHT). The mean sphericity is a measure of the roundness of the polymer particles and can be determined, for example, with the Camsizer® image analysis system (Retsch Technology GmbH; Germany).

The present invention is based on the finding that the polymer particles obtained by dropletization polymerization are hollow spheres and that the hollow spheres can be damaged by mechanical stress.

The coating according to the invention allows the mechanical stability of the hollow spheres to be increased significantly. Suitable coating agents are, for example, additives which increase the elasticity of the particle surface, for example by lowering the glass transition temperature, and/or mechanically solidify the particle surface.

The coating can be produced by coating the water-absorbing polymer particles prepared by dropletization polymerization in a known manner by mixing in the coating agent in the desired weight ratio. This coating takes place preferably in mixers with moving mixing tools, such as screw mixers, paddle mixers, disk mixers, plowshare mixers and shovel mixers. Particular preference is given to vertical mixers, very particular preference to plowshare mixers and shovel mixers. Suitable mixers are, for example, Lödige mixers, Bepex mixers, Nauta mixers, Processall mixers and Schugi mixers. Very particular preference is given to high-speed mixers, for example of the Schuggi-Flexomix or Turbolizer type. Very particular preference is also given to fluidized bed mixers.

The postcrosslinked water-absorbing polymer particles are preferably coated with water, an aqueous solution, an alkanolamine, a polymer and/or a wax.

The amount of water or aqueous solution used in the inventive coating is preferably from 1 to 30% by weight, more preferably from 2 to 20% by weight, most preferably from 3 to 15% by weight.

In a preferred embodiment in the case of coating with water or an aqueous solution, a surfactant is added as a deagglomerating assistant, for example sorbitan monoesters such as sorbitan monococoate and sorbitan monolaurate, or ethoxylated variants thereof. Further very suitable deagglomerating assistants are the ethoxylated and alkoxylated derivatives of 2-propylheptanol which are sold under the trademarks Lutensol® XL and Lutensol® XP (BASF Aktiengesellschaft, Germany).

The amount of the deagglomerating assistant used, based on the water-absorbing polymer particles, is, for example, from 0.01 to 1% by weight, preferably from 0.05 to 0.5% by weight, more preferably from 0.1 to 0.2% by weight.

The amount of alkanolamine used in the inventive coating is preferably from 0.5 to 30% by weight, more preferably from 1 to 20% by weight, most preferably from 2 to 15% by weight, and the alkanolamines can also be used as a solution in a suitable solvent, for example water.

Suitable alkanolamines are mono-, di- and trialkanolamines, such as ethanolamine, diethanolamine or triethanolamine. Preference is given to tertiary alkanolamines, such as triethanolamine, methyldiethanolamine, dimethylaminodiglycol, dimethylethanol-amine and N,N,N',N'-tetra(hydroxyethyl)ethylenediamine. Particular preference is given to triethanolamine.

The amount of polymer and/or wax is preferably from 0.005 to 10% by weight, more preferably from 0.05 to 5% by weight, most preferably from 0.1 to 2% by weight, based in each case on the polymer particles.

The polymer may also be applied to the particle surface by applying the precursors of the polymer to the particle surface, which do not react to give the desired polymer until they are on the particle surface, for example by reaction of polyols with polyepoxides.

The polymers, precursors thereof or waxes can be applied to the particle surface as aqueous dispersions, emulsions and/or polymer suspensions.

The polymers, precursors thereof or waxes may also be used in the form of a solution in an organic solvent or a mixture of water and an organic water-miscible solvent. These aqueous dispersions, emulsions and suspensions may also comprise a proportion of organic, possibly water-miscible solvents.

Suitable organic solvents are, for example, aliphatic and aromatic hydrocarbons such as n-hexane, cyclohexane, toluene and xylene, alcohols such as methanol, ethanol, isopropanol, ethylene glycol, propylene glycol, glycerol and polyethylene glycols with a mean molecular weight of from 200 to 10 000, ethers such as diethyl ether, esters such as ethyl acetate and n-butyl acetate, and ketones such as acetone and 2-butanone.

Suitable water-miscible organic solvents are, for example, aliphatic $C_1$- to $C_4$-alcohols, such as methanol, isopropanol, tert-butanol, ethylene glycol, propylene glycol, glycerol and polyethylene glycols having a mean molecular weight of from 200 to 10 000, ethers and ketones such as acetone and 2-butanone.

The polymers and/or waxes may also be metered in as a melt.

The polymers and/or waxes usable in the process according to the invention are preferably unreactive, i.e. they have no reactive groups which react with the groups on the surface of the polymer particles.

Preferred polymers and/or waxes are also especially those which do not tend to adhere within the temperature range between 0° C. and 80° C.

Preferred polymers to be used in accordance with the invention for the coating are homo- and copolymers of vinyl esters, especially vinyl acetate homopolymers and vinyl acetate copolymers with ethylene, acrylates, maleic esters, vinylamides and/or other vinyl acyl derivatives.

Preference is also given to homo- and copolymers of acrylic and methacrylic esters, for example copolymers of methyl methacrylate and n-butyl acrylate or 2-ethylhexyl acrylate.

These copolymers based on vinyl, acrylic and methacrylic esters may comprise, as further comonomers, for example, styrene, butadiene, vinylamides, olefinically unsaturated carboxylic acids and derivatives thereof, olefinically unsaturated sulfonic acids and derivatives thereof, vinylphosphonic acid and derivatives thereof or polyglycol esters of unsaturated acids.

Examples of vinylamides are in particular N-vinylformamide, N-vinyl-N-methylacetamide and N-vinylpyrrolidone.

Examples of olefinically unsaturated carboxylic acids are especially acrylic acid, methacrylic acid, itaconic acid and maleic acid, and also their alkali metal, ammonium and amine salts. Examples of derivatives of these olefinically unsaturated carboxylic acids are especially amides such as (meth)acrylamide, N-tert-butyl(meth)acrylamide and N-isopropyl(meth)acrylamide, but also N-methylolamides or ethers of N-methylolamides, monoamides and imides of aliphatic amines, and also acrylonitrile.

Examples of olefinically unsaturated sulfonic acids are the salts of vinylsulfonic acid, 2-acrylamido-2-methylpropanesulfonic acid, styrenesulfonic acid, allyl- and methallyl-sulfonic acid, especially their alkali metal, ammonium and amine salts.

Examples of derivatives of vinylphosphonic acid are especially the mono- and diesters of $C_1$- to $C_{18}$-alcohols, for example the methyl, propyl or stearyl esters. The vinyl-phosphonic acid itself is present in particular in the form of the mono- or disalt, preference being given to the alkali metal, ammonium and amine salts.

Polyglycol esters of unsaturated acids are in particular hydroxyethyl (meth)acrylate or esters of acrylic and methacrylic acid with polyalkylene oxide compounds of the general formula

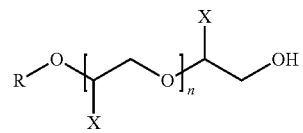

where
X is hydrogen or methyl,
n is from 0 to 50 and
R is an aliphatic, araliphatic or cycloaliphatic $C_1$ to $C_{24}$ radical, for example nonylphenyl.

In a preferred embodiment of the present invention, film-forming polymers are used for the coating. These are in particular polymers which have polymer films having a breaking resistance of from 0.5 to 25 N/mm, preferably from 1 to 20 N/mm, more preferably from 2 to 15 N/mm, most preferably from 5 to 10 N/mm, and an elongation at break of from 10 to 10 000%, preferably from 20 to 5000%, more preferably from 50 to 2000%, most preferably from 500 to 1000%. The breaking resistance and the elongation at break are determined to DIN EN ISO 527.

Preferred polymers to be used according to the invention for the coating are also film-forming polymers based on
  polyacetals, i.e. reaction products of polyvinyl alcohols with aldehydes such as butyraldehyde,
  polyurethanes, i.e. polymers obtainable by polyaddition from dihydric and higher polyhydric alcohols and isocyanates, for example prepared from polyester diols and/or polyether diols and, for example, 2,4- or 2,6-tolylene diisocyanate, 4,4-methylene di(phenylisocyanate) or hexamethylene diisocyanate (see Houben-Weyl, Methoden der Organischen Chemie [Methods of organic chemistry], 4th edition, Volume E20/2, pages 1561 to 1721),
  polyureas, i.e. polymers which are obtainable by polyaddition of diamines and diisocyanates or by polycondensation of diamines with carbon dioxide, phosgene, carboxylic esters (e.g. activated diphenyl carbonates) or urea, or by reacting diisocyanates with water (see Houben-Weyl, Methoden der Organischen Chemie, 4th edition, Volume E20/2, pages 1721 to 1752), polysiloxanes, the base polymer used being in particular linear dimethyl-polysiloxane whose end groups may have different modification (see "Chemie und Technologie des kalthärtenden Siliconkautschuks" [Chemistry and technology of cold-curing silicone rubber], pages 49 to 64 in SILICONE—Chemie und Technologie, [Symposium on Apr. 28, 1989] VULKAN-VERLAG, Essen), polyamides, preference being given to copolyamides (see Plaste Kautsch., Volume 25, pages 440 to 444 (1978)), as find use, for example, for the production of coatings, polyesters, i.e. polymers which are prepared by ring-opening polymerization of lactones or by polycondensation of hydroxycarboxylic acids or of diols and dicarboxylic acid derivatives (see Houben-Weyl, Methoden der Organischen Chemie, 4th edition, Volume E20/2, pages 1404 to 1429), epoxy resins which can be prepared from polyepoxides by polyaddition reactions with suitable hardeners or by polymerization via epoxy groups (see Houben-Weyl, Methoden der Organischen Chemie, 4th edition, Volume 14/2, pages 462 to 552 and Volume E20/2, pages 1891 to 1994 (for example reaction products of bisphenol A with epichlorohydrin)) or based on polycarbonates, as preparable easily by reacting diglycols or bisphenols with phosgene or carbonic diesters in polycondensation or transesterification reactions (see Houben-Weyl, Methoden der Organischen Chemie, 4th edition, Volume E 20/2, pages 1443 to 1457).

Particularly preferred polymers to be used in accordance with the invention for the coating are homo- and copolymers of acrylic and methacrylic esters, and also polymers based on polyacetals.

It is also possible to use mixtures of two or more of the abovementioned polymers. The mixing ratios are completely uncritical and should be adjusted to the particular circumstances.

Preferred polymers to be used in the process according to the invention are also elastic polymers. These are polymers with rubber-elastic behavior which can be elongated at 23° C. repeatedly to at least twice their length and, after removal of the force required for the elongation, immediately reassume their approximate starting length.

Representative examples of suitable elastic polymers are natural and synthetic latices which are typically used as binders and elastomeric adhesives in the production of air-drying absorbing products. In addition to the latices described in the examples, it is taken into account that any natural or synthetic elastomer suitable for the formation of a latex dispersion is suitable for use in the present invention. It is therefore possible to use natural rubber, polybutadiene rubber, styrene-butadiene rubber, arylnitrile-butadiene rubber, poly-2-chlorobutadiene rubber, polyisoprene rubber, isoprene-isobutylene copolymers, ethylene-propylene rubber, ethylene-vinyl acetate copolymers, chlorinated polyethylene, chlorosulfonated polyethylene, acrylic rubber, ethylene-acrylate copolymers, epichlorohydrin rubber, polypropylene oxide rubber and polyurethanes.

In a further preferred embodiment of the present invention, waxes are applied to the surface of the postcrosslinked water-absorbing polymer particles.

According to the formulation of the Deutschen Gesellschaft für Fettwissenschaft (DGF) [German Society for Fat Science] of 1974 (see DGF-Einheitsmethoden: Untersuchung von Fetten, Fettprodukten und verwandten Stoffen, Abteilung M: Wachse und Wachsprodukte [DGF standard methods: analysis of fats, fat products and related substances, division M: waxes and wax products]; Wissenschaftliche Verlagsgesellschaft, Stuttgart, 1975), a wax is understood in particular to mean a substance which, irrespective of its chemical composition and its natural or synthetic origin, is generally characterized by the following physicomechanical properties:

kneadable at 20° C., solid to brittle and hard;
coarsely to finely crystalline, transparent to opaque, but not grasslike;
melting above 40° C. without decomposition;
being of comparatively low viscosity even a little above the melting point and not stringing;
strongly temperature-dependent in consistency and solubility;
polishable under gentle pressure.

Preferred waxes are especially those whose melting and dropping points are within the temperature range between 30 and 180° C., more preferably between 40 and 180° C., most preferably between 40 and 170° C. The dropping point is determined by DGF standard method DGF-M-III 3 (75) (Wissenschaftliche Verlagsgesellschaft, Stuttgart).

Waxes to be used in accordance with the invention are, for example, natural waxes, modified natural waxes, semisynthetic waxes and fully synthetic waxes. Examples of natural waxes are recent waxes such as plant waxes or animal waxes. Examples of plant waxes are carnauba wax, candelilla wax, ouricury wax, sugarcane wax and retamo wax. Examples of animal waxes are insect waxes such as beeswax, ghedda wax and shellac wax, and also wool wax. Further examples of natural waxes are fossil waxes such as mineral oil waxes or brown coal waxes and peat waxes. Examples of mineral oil waxes are ozokerite and tank bottom wax; an example of a brown coal wax and peat wax is crude montan wax. Examples of modified natural waxes are the waxes obtained by refining, such as the macro- and microcrystalline paraffin waxes obtained from crude oil distillates or distillate residues, or chemically modified waxes such as double-bleached crude montan wax. Examples of semisynthetic waxes are the acid waxes and ester waxes preparable from montan wax, the wax acids producible by paraffin oxidation, and also alcohol waxes and amide waxes. Examples of fully synthetic waxes are hydrocarbon waxes such as polyolefin waxes and Fischer-Tropsch waxes, and also synthetic waxes having oxygen-functional groups. Examples of synthetic waxes with oxygen-functional groups are acid waxes which are formed by oxidizing synthetic hydrocarbon waxes or by copolymerizing or telomerizing olefins with unsaturated carboxylic acids, ester waxes which are obtained by esterifying synthetic wax acids with synthetic alcohols and by copolymerizing olefins with unsaturated esters such as vinyl acetate, alcohol waxes which are produced by an oxo process with subsequent hydrogenation and by hydrogenation of synthetic fatty acids, and also amide waxes which are obtained by reacting synthetic acids with amines. Examples of waxes which are obtained by oxidizing synthetic hydrocarbon waxes are oxidates of polyethylene waxes.

Preferred waxes to be used in accordance with the invention are refined (i.e. deresinified and bleached) montan waxes, and also polyolefin waxes.

Particularly preferred waxes to be used in accordance with the invention are polyolefin waxes such as polyethylene waxes (high-pressure polyethylene waxes, low-pressure polyethylene waxes, degraded polyethylene waxes), oxidates of these polyethylene waxes, waxes based on ethene-α-olefin copolymers, waxes based on ethylene-vinyl acetate copolymers, waxes based on ethylene-styrene copolymers, waxes based on ethylene-acrylic acid copolymers, and waxes based on wax mixtures of polyethylene waxes with poly(tetrafluoroethylene) waxes.

It is also possible to use mixtures of two or more of the abovementioned waxes. The mixing ratios are completely uncritical and should be adjusted to the particular circumstances.

The monomer solutions to be used in the process according to the invention to produce the water-absorbing polymer particles comprise at least one ethylenically unsaturated monomer a), optionally at least one crosslinker b), at least one initiator c) and water d).

The monomers a) are preferably water-soluble, i.e. the solubility in water at 23° C. is typically at least 1 g/100 g of water, preferably at least 5 g/100 g of water, more preferably at least 25 g/100 g of water, most preferably at least 50 g/100 g of water, and preferably have at least one acid group each.

Suitable monomers a) are, for example, ethylenically unsaturated carboxylic acids such as acrylic acid, methacrylic acid, maleic acid, fumaric acid and itaconic acid. Particularly preferred monomers are acrylic acid and methacrylic acid. Very particular preference is given to acrylic acid.

The preferred monomers a) have at least one acid group, the acid groups preferably being at least partly neutralized.

The proportion of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate, and mixtures thereof. Typically, the neutralization is achieved by mixing in the neutralizing agent as an aqueous solution, as a melt or preferably also as a solid. For example, sodium hydroxide with a water content significantly below 50% by weight may be present as a waxy material having a melting point above 23° C. In this case, metered addition as piece material or melt at elevated temperature is possible.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol is understood to mean compounds of the following formula

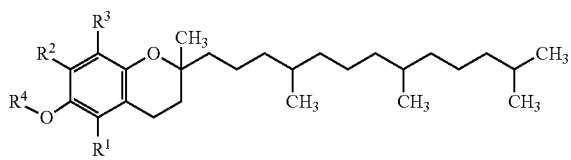

where $R^1$ is hydrogen or methyl, $R^2$ is hydrogen or methyl, $R^3$ is hydrogen or methyl, and $R^4$ is hydrogen or an acyl radical having from 1 to 20 carbon atoms.

Preferred radicals for $R^4$ are acetyl, ascorbyl, succinyl, nicotinyl and other physiologically compatible carboxylic acids. The carboxylic acids may be mono-, di- or tricarboxylic acids.

Preference is given to alpha-tocopherol where $R^1$=$R^2$=$R^3$=methyl, in particular racemic alpha-tocopherol. $R^1$ is more preferably hydrogen or acetyl. RRR-alpha-tocopherol is especially preferred.

The monomer solution comprises preferably at most 130 ppm by weight, more preferably at most 70 ppm by weight, preferably at least 10 ppm by weight, more preferably at least 30 ppm by weight, in particular around 50 ppm by weight, of hydroquinone monoether, based in each case on acrylic acid, acrylic acid salts also being considered as acrylic acid. For example, the monomer solution can be prepared by using acrylic acid having an appropriate content of hydroquinone monoether.

The polymerization inhibitors may also be removed from the monomer solution by absorption, for example on activated carbon.

Crosslinkers b) are compounds having at least two free-radically polymerizable groups which can be polymerized by a free-radical mechanism into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular N,N'-methylenebisacrylamide and N,N'-methylenebismethacrylamide, esters of unsaturated mono- or polycarboxylic acids of polyols, such as diacrylate or triacrylate, for example butanediol diacrylate, butane-diol dimethacrylate, ethylene glycol diacrylate or ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glycerol diallyl ether and glycerol triallyl ether, polyallyl ethers based on sorbitol, and ethoxylated variants thereof. In the process according to the invention, it is possible to use di(meth)acrylates of polyethylene glycols, the polyethylene glycol used having a molecular weight between 100 and 1000.

However, particularly advantageous crosslinkers b) are di- and triacrylates of 3- to 20-tuply ethoxylated glycerol, of 3- to 20-tuply ethoxylated trimethylolpropane, of 3- to 20-tuply ethoxylated trimethylolethane, in particular di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol or of 15-tuply ethoxylated trimethylolpropane, and also of at least 40-tuply ethoxylated glycerol, of at least 40-tuply ethoxylated trimethylolethane or of at least 40-tuply ethoxylated trimethylolpropane.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol.

The monomer solution comprises preferably at least 0.1% by weight, preferably at least 0.2% by weight, more preferably at least 0.3% by weight, most preferably at least 0.4% by weight, and preferably up to 2.5% by weight, preferentially up to 2% by weight, more preferably up to 1.5% by weight, most preferably up to 1% by weight, of crosslinker b), based in each case on monomer a).

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochloride and 2,2'-azobis[2-(5-methyl-2-imidazolin-2-yl)propane] dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/-hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)-phenyl]-2-hydroxy-2-methyl-1-propan-1-one, and mixtures thereof.

The initiators are used in customary amounts, for example in amounts of from 0.001 to 5% by weight, preferably from 0.01 to 1% by weight, based on the monomers a).

For optimal action, the preferred polymerization inhibitors require dissolved oxygen. Therefore, the monomer solution can be freed of dissolved oxygen before the polymerization by inertization, i.e. flowing through with an inert gas, preferably nitrogen. The oxygen content of the monomer solution is preferably lowered before the polymerization to less than 1 ppm by weight, more preferably to less than 0.5 ppm by weight.

The monomer solution is dropletized for polymerization in the gas phase.

The solids content of the monomer solution is preferably at least 35% by weight, preferably at least 38% by weight, more preferably at least 40% by weight, most preferably at least 42% by weight. The solids content is the sum of all constituents which are involatile after the polymerization. These are monomer a), crosslinker b) and initiator c).

The oxygen content of the gas phase is preferably from 0.001 to 0.15% by volume, more preferably from 0.002 to 0.1% by volume, most preferably from 0.005 to 0.05% by volume.

As well as oxygen, the gas phase preferably comprises only inert gases, i.e. gases which, under reaction conditions, do not intervene in the polymerization, for example nitrogen and/or steam.

The dropletization involves metering a monomer solution into the gas phase to form droplets. The dropletization of the monomer solution can be carried out, for example, by means of a dropletizer plate.

A dropletizer plate is a plate having at least one bore, the liquid entering the bore from the top. The dropletizer plate or the liquid can be oscillated, which generates a chain of ideally monodisperse droplets at each bore on the underside of the dropletizer plate.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The dropletizer is operated in the flow range of laminar jet decomposition, i.e. the Reynolds number based on the throughput per bore and the bore diameter is preferably less than 2000, preferentially less than 1000, more preferably less than 500 and most preferably less than 100. The pressure drop through the bore is preferably less than 2.5 bar, more preferably less than 1.5 bar and most preferably less than 1 bar.

The dropletizer plate has typically at least one bore, preferably at least 10, more preferably at least 50 and typically up to 10 000 bores, preferably up to 5000, more preferably up to 1000 bores, the bores typically being distributed uniformly over the dropletizer plate, preferably in so-called triangular pitch, i.e. three bores in each case form the corners of an equilateral triangle.

The diameter of the bores is adjusted to the desired droplet size. The droplets generated have a mean droplet size of preferably at least 100 µm, more preferably of at least 150 µm, most preferably of at least 200 µm, the droplet diameter being determinable by light scattering.

It may be advantageous to place the dropletizer plate onto a carrier plate, in which case the carrier plate likewise has bores. In this case, the bores of the carrier plate have a greater diameter than the bores of the dropletizer plate and are arranged such that below each bore of the dropletizer plate is disposed a concentric bore of the carrier plate. This arrangement enables a rapid exchange of the dropletizer plate, for example in order to generate droplets of another size.

However, the dropletization can also be carried out by means of pneumatic drawing dies, rotation, cutting of a jet or rapidly actuable microvalve dies.

In a pneumatic drawing die, a liquid jet together with a gas stream is accelerated through a diaphragm. The gas rate can be used to influence the diameter of the liquid jet and hence the droplet diameter.

In the case of dropletization by rotation, the liquid passes through the orifices of a rotating disk. As a result of the centrifugal force acting on the liquid, droplets of defined size are torn off. Preferred apparatus for rotary dropletization are described, for example, in DE 43 08 842 A1.

The emerging liquid jet can also be cut into defined segments by means of a rotating blade. Each segment then forms a droplet.

In the case of use of microvalve dies, droplets with defined liquid volumes are generated directly.

The gas phase preferably flows as carrier gas through the reaction chamber. The carrier gas can be conducted through the reaction chamber in cocurrent or in counter-current to the free-falling droplets of the monomer solution, preferably in cocurrent. After one pass, the carrier gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The gas velocity is preferably adjusted such that the flow in the reactor is directed, for example no convection currents opposed to the general flow direction are present, and is, for example, from 0.01 to 5 m/s, preferably from 0.02 to 4 m/s, more preferably from 0.05 to 3 m/s, most preferably from 0.1 to 2 m/s.

The carrier gas is appropriately preheated to the reaction temperature upstream of the reactor.

The reaction temperature in the thermally induced polymerization is preferably from 70 to 250° C., more preferably from 100 to 220° C. and most preferably from 120 to 200° C.

The reaction can be carried out under elevated pressure or under reduced pressure; preference is given to a reduced pressure of up to 100 mbar relative to ambient pressure.

The reaction offgas, i.e. the carrier gas leaving the reaction chamber, may, for example, be cooled in a heat exchanger. This condenses water and unconverted monomer a). The reaction offgas can then be reheated at least partly and recycled into the reactor as cycle gas. A portion of the reaction offgas can be discharged and replaced by fresh carrier gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated. In this case, the trace heating is adjusted such that the wall temperature is at least 5° C. above the internal reactor temperature and condensation on the reactor walls is reliably prevented.

The reaction product can be withdrawn from the reactor in a customary manner, preferably at the bottom by means of a conveying screw, and, if appropriate, dried down to the desired residual moisture content and to the desired residual monomer content.

The polymer particles are subsequently postcrosslinked for further improvement of the properties. Suitable postcrosslinkers are compounds which comprise at least two groups which can form covalent bonds with the carboxylate groups of the hydrogel. Suitable compounds are, for example, alkoxysilyl compounds, polyaziridines, polyamines, polyamidoamines, di- or polyepoxides, as described in EP 83 022 A2, EP 543 303 A1 and EP 937 736 A2, di- or polyfunctional alcohols as described in DE 33 14 019 A1, DE 35 23 617 A1 and EP 450 922 A2, or β-hydroxyalkylamides, as described in DE 102 04 938 A1 and U.S. Pat. No. 6,239,230.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1199 327 A2 describes oxetanes and cyclic ureas, and WO 2003/31482 A1 describes morpholine-2,3-dione and its derivatives, as suitable postcrosslinkers.

It is also possible to use postcrosslinkers which comprise additional polymerizable ethylenically unsaturated groups, as described in DE 37 13 601 A1.

The amount of postcrosslinker is preferably from 0.01 to 1% by weight, more preferably from 0.05 to 0.5% by weight, most preferably from 0.1 to 0.2% by weight, based in each case on the polymer.

In a preferred embodiment of the present invention, polyvalent cations are applied to the particle surface in addition to the postcrosslinkers.

The polyvalent cations usable in the process according to the invention are, for example, divalent cations such as the cations of zinc, magnesium, calcium and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate is preferred.

The amount used, based on the polymer particles, is, for example, from 0.001 to 0.5% by weight, preferably from 0.005 to 0.2% by weight, more preferably from 0.02 to 0.1% by weight.

The postcrosslinking is typically performed in such a way that a solution of the postcrosslinker is sprayed onto the hydrogel or the dry polymer particles. The spraying is followed by thermal drying, and the postcrosslinking reaction can take place either before or during the drying.

The spraying of a solution of the crosslinker is preferably performed in mixers with moving mixing tools, such as screw mixers, paddle mixers, disk mixers, plowshare mixers and shovel mixers. Particular preference is given to vertical mixers, very particular preference to plowshare mixers and shovel mixers. Suitable mixers are, for example, Lödige mixers, Bepex mixers, Nauta mixers, Processall mixers and Schugi mixers.

The thermal drying is preferably carried out in contact dryers, more preferably shovel dryers, most preferably disk dryers. Suitable dryers are, for example, Bepex dryers and Nara dryers. Moreover, it is also possible to use fluidized bed dryers.

The drying can be effected in the mixer itself, by heating the jacket or blowing in warm air. Equally suitable is a downstream dryer, for example a staged dryer, a rotary tube oven or a heatable screw. It is particularly advantageous to mix and dry in a fluidized bed dryer.

Preferred drying temperatures are in the range from 100 to 250° C., preferably from 120 to 220° C. and more preferably from 140 to 200° C. The preferred residence time at this temperature in the reaction mixer or dryer is preferably at least 10 minutes, more preferably at least 20 minutes, most preferably at least 30 minutes.

The process according to the invention enables the preparation of water-absorbing polymer particles with a high centrifuge retention capacity (CRC), a high absorption under a pressure of 4.83 kPa (AUP0.7 psi) and high mechanical stability.

The water-absorbing polymer particles obtainable by the process according to the invention typically have the form of hollow spheres. The present invention therefore further provides water-absorbing polymer particles comprising at least one cavity in the particle interior and at least 1% by weight of water and/or at least one alkanolamine, the crosslinking density at the particle surface having been increased.

The water content of the inventive polymer particles is preferably from 1 to 30% by weight, more preferably from 2 to 20% by weight, most preferably from 3 to 15% by weight.

The inventive polymer particles comprise preferably from 0.5 to 30% by weight, more preferably from 1 to 20% by weight, most preferably from 2 to 15% by weight, of at least one alkanolamine.

The inventive water-absorbing polymer particles are approximately round, i.e. the polymer particles have a mean sphericity (mSPHT) of typically at least 0.84, preferably at least 0.86, more preferably at least 0.88 and most preferably at least 0.9. The sphericity (SPHT) is defined as $$SPHT = \frac{4\pi A}{U^2},$$

where A is the cross-sectional area and U is the cross-sectional circumference of the polymer particles. The mean sphericity (mSPHT) is the volume-average sphericity.

The mean sphericity (mSPHT) can be determined, for example, with the Camsizer® image analysis system (Retsch Technology GmbH; Germany).

Polymer particles with relatively low mean sphericity (mSPHT) are obtained by reverse suspension polymerization when the polymer particles are agglomerated during or after the polymerization.

The water-absorbing polymer particles prepared by customary solution polymerization (gel polymerization) are ground and classified after drying to obtain irregular polymer particles. The mean sphericity (mSPHT) of these polymer particles is between approx. 0.72 and approx. 0.78.

The present invention further provides water-absorbing polymer particles comprising at least one cavity in the particle interior, the crosslinking density at the particle surface having been increased, the particles having a mean sphericity (mSPHT) of at least 0.84, preferably of at least 0.86, more preferably of at least 0.88, most preferably of at least 0.9, and the particles having an absorption index (AUP0.7 psi index) of at least 60%, preferably of at least 70%, more preferably of at least 80%, most preferably of at least 85%.

The present invention further provides water-absorbing polymer particles comprising at least one cavity in the particle interior, the crosslinking density at the particle surface having been increased, having a mean sphericity (mSPHT) of at least 0.84, preferably of at least 0.86, more preferably of at least 0.88, most preferably of at least 0.9, and a stability index of less than 0.15, preferably of less than 0.10, more preferably of less than 0.075, most preferably of less than 0.05.

The water content of the water-absorbing polymer particles is typically less than 10% by weight, preferably less than 8% by weight, more preferably less than 6% by weight, most preferably less than 4% by weight, the water content being determined by the EDANA (European Disposables and Nonwovens Association) recommended test method No. WSP 230.2-05 "Moisture content".

The ratio of maximum diameter of the cavity to maximum diameter of the polymer particle is preferably at least 0.1, more preferably at least 0.3, most preferably at least 0.4.

The polymer particles comprise preferably at least 50 mol %, more preferably at least 90 mol %, most preferably at least 95 mol %, of polymerized acrylic acid. The polymerized acrylic acid has preferably been neutralized to an extent of from 25 to 85 mol %, more preferably to an extent of from 50 to 80 mol %, most preferably to an extent of from 60 to 75 mol %.

The present invention further provides water-absorbing polymer particles which are obtainable by the process according to the invention.

The water-absorbing polymer particles obtainable by the process according to the invention have a centrifuge retention capacity (CRC) of typically at least 20 g/g, preferably at least 25 g/g, preferentially at least 30 g/g, more preferably at least 35 g/g, most preferably at least 40 g/g. The centrifuge retention capacity (CRC) of the water-absorbing polymer particles is typically less than 60 g/g.

The water-absorbing polymer particles obtainable by the process according to the invention have an absorption under a pressure of 4.83 kPa (AUP0.7 psi) of typically at least 15 g/g, preferably at least 20 g/g, more preferably of at least 25 g/g, most preferably of at least 30 g/g. The absorption under a pressure of 4.83 kPa (AUP0.7 psi) of the water-absorbing polymer particles is typically less than 50 g/g.

The water-absorbing polymer particles obtainable by the process according to the invention have a permeability (SFC) of typically at least $2 \times 10^{-7}$ cm$^3$s/g, preferably at least $10 \times 10^{-7}$ cm$^3$s/g, more preferably at least $30 \times 10^{-7}$ cm$^3$s/g, even more preferably at least $60 \times 10^{-7}$ cm$^3$s/g, most preferably at least $200 \times 10^{-7}$ cm$^3$s/g. The permeability (SFC) of the water-absorbing polymer particles is usually less than $500 \times 10^{-7}$ cm$^3$s/g.

The mean diameter of the polymer particles is preferably at least 200 μm, more preferably from 250 to 600 μm, very particularly from 300 to 500 μm, the particle diameter being determinable by light scattering and meaning the volume-average mean diameter. 90% of the polymer particles have a diameter of preferably from 100 to 800 μm, more preferably from 150 to 700 μm, most preferably from 200 to 600 μm.

The present invention further provides processes for producing hygiene articles, especially diapers, comprising the use of water-absorbing polymer particles produced by the abovementioned process.

The present invention further provides for the use of inventive water-absorbing polymer particles in hygiene articles, for thickening wastes, especially medical wastes, or as a water-retaining agent in market gardening.

The water-absorbing polymer particles are tested by means of the test methods described below.

Methods:

The measurements should, unless stated otherwise, be performed at an ambient temperature of 23±2° C. and a relative air humidity of 50±10%. The water-absorbing polymers are mixed thoroughly before the measurement.

Mean Sphericity (mSPHT)

The mean sphericity (mSPHT) is determined with the Camsizer® image analysis system (Retsch Technology GmbH; Germany).

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameter designated as sphericity in the program is employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. The equivalent diameter $xc_{min}$ corresponds to the mesh size of a screen that the particle can just pass through. To record the particles, the so-called CCD-zoom camera (CAM-Z) is used. To control the metering channel, a surface coverage fraction of 0.5% is predefined.

Water Content

The water content of the water-absorbing polymer particles is determined by the EDANA (European Disposables and Nonwovens Association) recommended test method No. WSP 230.2-05 "Moisture content".

Centrifuge Retention Capacity (CRC Centrifuge Retention Capacity)

The centrifuge retention capacity of the water-absorbing polymer particles is determined by the EDANA (European Disposables and Nonwovens Association) recommended test method No. WSP 241.2-05 "Centrifuge retention capacity".

Absorption Under Pressure (AUP0.7 psi Absorption Under Pressure)

The absorption under pressure is determined by the EDANA (European Disposables and Nonwovens Association) recommended test method No. WSP 242.2-05 "Absorption under pressure", using a weight of 49 g/cm² (0.7 psi) instead of a weight of 21 g/cm² (0.3 psi).

Saline Flow Conductivity (SFC)

The saline flow conductivity of a swollen gel layer under a load of 0.3 psi (2070 Pa) is, as described in EP 640 330 A1, determined as the gel layer permeability of a swollen gel layer of water-absorbing polymer particles, except that the apparatus described on page 19 and in FIG. 8 in the aforementioned patent application was modified to the effect that the glass frit (40) is no longer used, the plunger (39) consists of the same polymer material as the cylinder (37) and now comprises 21 bores of equal size distributed uniformly over the entire contact surface. The procedure and evaluation of the measurement remain unchanged from EP 640 330 A1. The flow rate is recorded automatically.

The saline flow conductivity (SFC) is calculated as follows:

$$SFC\ [cm^3 s/g] = (Fg(t=0) \times L0)/(d \times A \times WP),$$

where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in g/cm³, A is the surface area of the gel layer in cm², and WP is the hydrostatic pressure over the gel layer in dyn/cm².

Absorption Index (AUP0.7 psi Index)

The absorption index (AUP0.7 psi index) describes the mechanical stability of the water-absorbing polymer particles.

To this end, 20 g of water-absorbing polymer particles are weighed into a cylindrical porcelain mill with a capacity of approx. 360 ml. The porcelain mill has an internal length of 8.8 cm and an internal diameter of 7.2 cm. In addition, 24 cylindrical porcelain bodies are introduced. The porcelain bodies have a height of 1.25 cm and a diameter of 1.25 cm. The weight of one porcelain body is 5.3 g. The cylindrical porcelain mill is closed and rolled by means of a roller-driven system at 150 revolutions per minute for 15 minutes.

The absorption under pressure (AUP0.7 psi) of the water-absorbing polymer particles is measured before and after mechanical stress.

The absorption index (AUP0.7 psi index) is calculated as follows:

$$AUP0.7\ psi\ index = AUP0.7\ psi_{after}/AUP0.7\ psi_{before} \times 100\%$$

where AUP0.7 $psi_{before}$ is the absorption under pressure (AUP0.7 psi) of the polymer particles before the mechanical stress and AUP0.7 $psi_{after}$ is the absorption under pressure (AUP0.7 psi) of the polymer particles after the mechanical stress.

Stability Index

The stability index describes the mechanical stability of the water-absorbing polymer particles.

The mechanical stress is carried out as already described for the absorption index.

The proportion of water-absorbing polymer particles having a particle size of less than 100 µm is measured before and after the mechanical stress. When the water-absorbing polymer particles comprise more than 1% by weight of particles having a particle size of less than 100 µm, these should be removed beforehand.

The stability index is calculated as follows:

$$\text{Stability index} = (\text{particles} < 100\ \mu m_{after} - \text{particles} < 100\ \mu m_{before})/100\%\ \text{by wt.}$$

where particles<100 $\mu m_{before}$ is the proportion by weight of polymer particles having a particle size of less than 100 µm before the mechanical stress and particles<100 $\mu m_{after}$ is the proportion by weight of polymer particles having a particle size of less than 100 µm after the mechanical stress.

The particles having a particle size of less than 100 µm are determined photooptically with a PartAn 2001 F/L particle analyzer (from AnaTec, Duisburg, Germany). For the measurement, 20 g of polymer particles are used.

EXAMPLES

Example 1

14.3 kg of sodium acrylate (37.5% by weight solution in water) and 1.6 kg of acrylic acid were mixed with 29 g of 15-tuply ethoxylated trimethylolpropane triacrylate. The solution was dropletized into a heated dropletization tower filled with a nitrogen atmosphere (180° C., height 12 m, width 2 m, gas velocity 0.1 m/s in cocurrent). The metering rate was 16 kg/h. The dropletizer plate had 30×170 µm bores. The diameter of the dropletizer plate was 65 mm. The initiator was mixed with the monomer solution just upstream of the dropletizer by means of a static mixer. The initiator used was a 6.5% by weight solution of 2,2'-azobis[2-(2-imidazolin-2-yl) propane] dihydrochloride in water. The metering rate of the initiator solution was 0.44 kg/h. The gas outlet temperature from the dropletization tower was 126° C.

Subsequently, the resulting water-absorbing polymer particles were postcrosslinked. To this end, 200 g of water-absorbing polymer particles were sprayed with 6.3 g of postcrosslinker solution by means of a two-substance nozzle in a food processor at a medium stirrer level. The postcrosslinker solution consisted of 0.3 g of 2-hydroxyethyl-2-oxazolidone, 4.2 g of water and 1.8 g of isopropanol. The moist polymer was homogenized once again with a spatula and heat-treated at 170° C. in a forced-air drying cabinet for 90 minutes. The postcrosslinked polymer particles were freed of lumps by means of an 850 µm screen.

Example 2

The postcrosslinked water-absorbing polymer particles obtained according to Example 1 were coated. To this end, 200 g of postcrosslinked water-absorbing polymer particles were preheated at 80° C. in a heated cabinet for at least 30 minutes and sprayed with the coating agent by means of a two-substance nozzle in a food processor at a medium stirrer level. The coating agent used was 8.0 g of water. Stirring was continued for one minute. After storage for 16 hours, the coated polymer particles were freed of lumps by means of an 850 µm screen.

The results are summarized in Table 1.

Example 3

The procedure of Example 2 was repeated. The coating agent used was a solution of 8.0 g of water and 0.306 g of sorbitan monolaurate.

The results are summarized in Table 1.

Example 4

The procedure of Example 2 was repeated. The coating agent used was a solution of 8.0 g of water, 0.306 g of sorbitan monolaurate and 3.0 g of triethanolamine. The results are summarized in Table 1.

Example 5

The procedure of Example 2 was repeated. The coating agent used was a solution of 8.0 g of water, 0.306 g of sorbitan monolaurate and 6.0 g of triethanolamine.

The results are summarized in Table 1.

TABLE 1

Analysis results

| Ex. | AUP 0.7 psi (before) | AUP 0.7 psi (after) | AUP 0.7 psi index | Particles < 100 µm (before) | Particles < 100 µm (after) | Stability index |
|---|---|---|---|---|---|---|
| 1*) | 24.7 g/g | 12.8 g/g | 51.8% | 0.2% by weight | 30.9% by weight | 0.31 |
| 2 | 24.2 g/g | 16.4 g/g | 67.9% | 0.1% by weight | 20.3% by weight | 0.20 |
| 3 | 24.1 g/g | 19.0 g/g | 78.8% | 0.1% by weight | 6.6% by weight | 0.065 |
| 4 | 23.6 g/g | 18.4 g/g | 78.0% | 0.1% by weight | 6.6% by weight | 0.065 |
| 5 | 22.8 g/g | 19.4 g/g | 85.1% | 0.1% by weight | 4.8% by weight | 0.047 |

*)comparative example

The invention claimed is:

1. A process for producing water-absorbing polymer particles comprising (i) polymerizing droplets of a monomer solution comprising
   a) at least one ethylenically unsaturated monomer,
   b) optionally at least one crosslinker,
   c) at least one initiator,
   d) water,
in a gas phase surrounding the droplets, (ii) the resulting polymer particles being postcrosslinked, then (iii) at least partly coating the postcrosslinked polymer particles with water or an aqueous solution comprising sorbitan monoester and/or an alkanolamine.

2. The process according to claim 1, wherein a solids content of the monomer solution is at least 35% by weight.

3. The process according to claim 1, wherein the monomer a) is at least partly neutralized acrylic acid to an extent of at least 50 mol %.

4. The process according to claim 1, wherein the droplets have a mean diameter of at least 100 µm.

5. Water-absorbing polymer particles produced according to claim 1.

6. Water-absorbing polymer particles according to claim 5 comprising at least one cavity in the particle interior and at least 1% by weight of water and/or at least one alkanolamine, a crosslinking density at the particle surface having been increased.

7. The polymer particles according to claim 5, wherein the polymer particles have a mean sphericity of at least 0.84.

8. Water-absorbing polymer particles according to claim 5 comprising at least one cavity in the particle interior, a crosslinking density at the particle surface having been increased, and the particles having a mean sphericity of at least 0.84 and an absorption index of at least 60%.

9. Water-absorbing polymer particles according to claim 5 comprising at least one cavity in the particle interior, a crosslinking density at the particle surface having been increased, and the particles having a mean sphericity of at least 0.84 and a stability index of less than 0.15.

10. The polymer particles according to claim 5, which have at least one cavity and wherein a ratio of maximum diameter of the cavity to maximum diameter of the polymer particle is at least 0.1.

11. The polymer particles according to claim 5, which comprise at least partially neutralized polymerized acrylic acid to an extent of at least 50 mol %.

12. The polymer particles according to claim 5, wherein the polymer particles have an absorption under pressure (AUP0.7 psi) of at least 15 g/g.

13. The polymer particles according to claim 5, which have a mean diameter of at least 200 µm.

14. A hygiene article comprising polymer particles according to claim 5.

15. The polymer particles according to claim 6, wherein the polymer particles have a mean sphericity of at least 0.84.

* * * * *